(12) United States Patent
Chanbasha et al.

(10) Patent No.: US 9,568,460 B2
(45) Date of Patent: Feb. 14, 2017

(54) SIMPLE METHOD FOR THE DETECTION OF SULFUR COMPOUNDS IN CRUDE OILS AND DIESEL

(71) Applicants: King Fahd University of Petroleum and Minerals, Dhahran (SA); King Abdulaziz City for Science and Technology, Riyadh (SA)

(72) Inventors: Basheer Chanbasha, Dhahran (SA); Ibrahim Mohammed Al-Zahrani, Dammam (SA); Than Htun, Dhahran (SA)

(73) Assignees: King Fahd University of Petroleum and Minerals, Dhahran (SA); King Abdulaziz City for Science and Technology, Riyadh (SA)

(*) Notice: Subject to any disclaimer, the term of this patent is extended or adjusted under 35 U.S.C. 154(b) by 421 days.

(21) Appl. No.: 14/471,956

(22) Filed: Aug. 28, 2014

(65) Prior Publication Data
US 2016/0061804 A1 Mar. 3, 2016

(51) Int. Cl.
*G01N 30/62* (2006.01)
*G01N 33/28* (2006.01)
(Continued)

(52) U.S. Cl.
CPC .......... *G01N 33/287* (2013.01); *G01N 30/02* (2013.01); *G01N 30/14* (2013.01); *G01N 30/88* (2013.01);
(Continued)

(58) Field of Classification Search
CPC .. G01N 33/287; G01N 33/28; G01N 33/2835; G01N 30/14; G01N 2030/146; G01N 2030/8854; G01N 30/88; G01N 1/4055; G01N 2001/4061
(Continued)

(56) References Cited

U.S. PATENT DOCUMENTS

| | | | | |
|---|---|---|---|---|
| 4,844,804 A | * | 7/1989 | Taylor | B01D 17/085 210/321.8 |
| 5,744,702 A | * | 4/1998 | Roussis | G01N 33/287 73/53.01 |

(Continued)

FOREIGN PATENT DOCUMENTS

CN  101376070 B  11/2010

OTHER PUBLICATIONS

Ibrahim M Zahrani, "Determination of sulfur compounds in crude oil using liquid-phase microextraction" Aug. 22, 2012, 244[th]ACS National Meeting, Philadelphia, PA. http://abstracts.acs.org/chem/244nm/program/divisionindex.php?ni=1&act=presentations&val=Heavy+Hydrocarbon+Resources%3A+Characterization%2C+Upgrading+and+Utilization&ses=Heavy+Hydrocarbon+Resources%3A+Characterization%2C+Upgrading+and+Utilization&prog=114499.

(Continued)

*Primary Examiner* — Benjamin Schmitt
(74) *Attorney, Agent, or Firm* — Oblon, McClelland, Maier & Neustadt, L.L.P.

(57) ABSTRACT

A liquid phase microextraction (LPME) method was developed for the determination of sulfur compounds in crude oils and its fractions (e.g diesel). Wide ranges of sulfur compounds including benzothiophene, dibenzothiophene and their derivatives were used as model compounds for extraction. After extraction, the analyses were performed by gas chromatography equipped with sulfur chemiluminescence detector (GC-SCD). Various experiments conditions influencing the extraction such as extraction times, extraction solvents, solvent volume and quantitative parameters were optimized to achieve higher extraction efficiency and high accuracy. The optimized conditions were applied to the determination of sulfur compounds in crude oil and diesel.

20 Claims, 4 Drawing Sheets

(51) Int. Cl.
  *G01N 30/02* (2006.01)
  *G01N 33/00* (2006.01)
  *G01N 30/14* (2006.01)
  *G01N 30/88* (2006.01)
  *G01N 21/76* (2006.01)
  *G01N 30/74* (2006.01)
  *G01N 1/40* (2006.01)
  *G01N 30/00* (2006.01)
(52) U.S. Cl.
  CPC ......... *G01N 33/0044* (2013.01); *G01N 1/4055* (2013.01); *G01N 21/766* (2013.01); *G01N 30/74* (2013.01); *G01N 2001/4061* (2013.01); *G01N 2030/009* (2013.01); *G01N 2030/146* (2013.01); *G01N 2030/8854* (2013.01)
(58) Field of Classification Search
  USPC ............... 73/61.41, 61.52, 61.58, 61.61, 61.63, 73/61.68
  See application file for complete search history.

(56) References Cited

U.S. PATENT DOCUMENTS

2008/0165361 A1* 7/2008 Kauffman ............ G01N 33/287
  356/402
2013/0084646 A1* 4/2013 Green ................ G01N 30/7206
  436/173

OTHER PUBLICATIONS

Mahdi Hashemi, et al., "Determination of volatile organochalcogens using liquid phase microextraction and gas chromatography with fluorine-induced chemiluminescence detection." Feb. 2013, Environmental Biotechnology, 2012, 8(2) p. 55-62.

* cited by examiner

SIMPLE METHOD FOR THE DETECTION OF SULFUR COMPOUNDS IN CRUDE OILS AND DIESEL

BACKGROUND OF THE INVENTION

Technical Field

The present invention relates to a hollow fiber membrane supported liquid-phase microextraction (HFM-LPME) method for determining sulfur compound concentration in a hydrocarbon sample and a hollow fiber membrane supported liquid-phase microextraction (HFM-LPME) system for determining sulfur compound concentration in a hydrocarbon sample.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Fossil fuel is the main source of world wide's energy, petroleum products such as diesel is extensively used as a fuel for transportation systems (C. Song, Catalysis Today 86 (2003) 211; J. H. Kim, X. Ma, A. Zhon, C. Song, Catal Today 111 (2006) 74—each incorporated herein by reference in its entirety). Crude oil consists of more than 200 sulfur compounds which includes derivatives of thiophenes and benzothiophene in the range of 0.01 to 3% as a total sulfur (C. Song, X. Ma, Appl. Catal. B Environmental, 41 (2003) 207; P. T. Vasudevan, J. L. Firrro, Catalysis Rev.—Science Eng. 38(1996)161; M. R. Gary F. Khorasheh, Ind. Eng. Chem, 17 (1978) 196; S. Zhang, D. Liue, W. Deng, Energy Fuels 21 (2007) 3057—each incorporated herein by reference in its entirety). The sulfur content in petroleum product increases along with the boiling points of the distillate fractions (P. S. Tam, J. W. Eldridge, Ind. Eng. Chem. Res. 29 (1990) 321; A. Stanislaus, A. Marafi, M. S. Rana, Catalysis Today 153, (2010) 1—each incorporated herein by reference in its entirety). The sulfur compounds in petroleum products significantly damage the environmental and also leads to undesirable effects in refining processes such as deactivation of catalysts (A. Marafi, A. Al-Hindi, A. Stanislaus, Fuel Process. Technol. 88 (2007) 905; X. L. Ma, K. Sakanishi, I. Mochida, Ind. Eng. Chem. Res. 34 (1995) 748—each incorporated herein by reference in its entirety). Sulfur compounds generate SOx and particulate emissions during combustion process (X. Ma, S. Velu, J. H. Kim, C. Song, Appl. Catal. B Environ. 56 (2005)137; M. M. Mariq, R. E. Chase, N. Xu, P. M. Laing, Environ. Sci. Technol., 36 (2002) 283; A. Sydbom, A. Blomberg, S. Parnia, N. Stenfors, T. Sandstrom, S.- E. Dahlen, Eur. Respir. J. 17 (2001) 733; I. Vergov, I. Shishkova, Petrol. Coal. 51 (2009) 136—each incorporated herein by reference in its entirety). The presence of SOx in the exhaust gas is also one of the leading causes of acid rain (L. Hylander, M. Goodsite, Sci. Tot. Environ. 368 (2006) 352; Y. Shiraishi, T. Hirari, Eng. Chem. Res. 37 (1998) 218—each incorporated herein by reference in its entirety). To improve the air quality, environmental regulations have been implemented in many parts of the world to reduce the SOx by restricting the emission level to less than 10 mg $L^{-1}$ (N. Gupta, P. Roychoudhury, Appl. Microbiol. Biotechnol. 66 (2005) 356; F. Ali, A. Malki, Fuel Process. Technol. 42 (1995) 35; J. D. Holbery, K. R. Seddon, Green Chem 10 (2008) 87; S. T. Oyama, J. Catal. 216 (2003) 343—each incorporated herein by reference in its entirety). Analytical methods capable of detecting sulfur in low concentrations from complex sample matrices are highly demanding.

Quantitative determination of sulfur compounds in crude oils are a challenging task due to the complicated sample matrix. The American Petroleum Institute (API) gravity and viscosity of are higher for crude oils and diesel, traditional sample preparation methods are not effective. Based on the physical and chemical properties of the samples several American Society for Testing and Materials (ASTM) methods based on gas chromatography methods have been reported for quantitative measurement of sulfur compounds (C. L. Hemler, L. F. Smith, in: R. A. Meyers (Ed.), Handbook of Petroleum Refining Processes, McGraw-Hill, 2004—incorporated herein by reference in its entirety). To avoid the sample preparation prior to sample introduction into GC system, crude oils were simply diluted with organic solvents (P. K. Niccum, C. R. Santner, in: R. A. Meyers (Ed.), Handbook of Petroleum Refining Processes, McGraw-Hill, Texas, 2004—incorporated herein by reference in its entirety). The metallic constituents (Ni and V could be as high as 1000 μg $g^{-1}$) that also cause the greatest concern for GC analysis (J. G. Speight, The Chemistry and Technology of Petroleum, Taylor & Francis, New York, 2006—incorporated herein by reference in its entirety). Selectivity of the ASTM method relates on the instrumental conditions for example, ASTM D5623, ASTM D3328, ASTM D6228 methods were reported for sulfur analysis in petrochemical matrices using GC with pulsed flame photometric detector (PFPD) and ASTM D5504 was reported for GC with sulfur chemiluminescence detection (Determination of Sulfur Compounds in Natural Gas and Gaseous Fuels by Gas Chromatography and Chemiluminescence, ASTM D5504 (05.06), ASTM, Philadelphia, Pa., 2002; ASTM Standard D 3328-06, Standard Test Method for Comparison of Waterborne Petroleum Oils by Gas Chromatography, ASTM International, West Conshohocken, Pa., www.astm.org; ASTM Standard D 6228-98, Standard Test Method for Determination of Sulfur Compounds in Natural Gas and Gaseous Fuels by Gas Chromatography and Flame Photometric Detection, ASTM International, West Conshohocken, Pa., www.astm.org; ASTM Standard D 5623-94, Standard Test Method for Sulfur Compounds in Light Petroleum Liquids by Gas Chromatography and Sulfur Selective Detection, ASTM International, West Conshohocken, Pa., www.astm.org; ASTM Standard D 5623-94, Standard Test Method for Sulfur Compounds in Light Petroleum Liquids by Gas Chromatography and Sulfur Selective Detection, ASTM International, West Conshohocken, Pa., www.astm.org—each incorporated herein by reference in its entirety). All these ASTM methods, samples were directly analyzed with series of dilutions. Large volume dilution may lead to poor quantitation and the particulates in crude oil might contaminate the GC injection port (Paola A. Mello, Juliana S. F. Pereira, Marcia F. Mesko, Juliano S. Barin, Erico M. M. Flores, Anal. Chim. Acta. 746 (2012) 15—incorporated herein by reference in its entirety).

More environmentally-friendly alternatives to conventional methods have been disclosed for determination of sulfur compounds in other sample matrices which includes solid-phase microextraction, dispersive liquid-liquid microextraction, and solid-phase extraction (U. C. Meier, J. Chromatogr. A. 1286 (2013) 159; V. P. Jofré, M. V. Assof, M. L. Fanzone, H. C. Goicoechea, L. D. Martinez, M. F. Silva, Anal. Chim. Acta. 683 (2010) 126; E. Kabir, K- H. Kim, Microchem. J. 103 (2012) 42—each incorporated herein by reference in its entirety). However, these methods have not been investigated for the complex sulfur compound detection in complex sample matrices such as crude oil and heavy diesel samples.

Hollow fiber membrane supported liquid-phase microextraction (HFM-LPME) has been reported for extraction of various classes of analytes from various complex sample matrices such as beverages, urine, soil, waste water, and oil spills in sediment samples (Xiong J, Hu B. J Chromatogr A. 1193 (2008) 7; Li Xu, C. Basheer, H. K. Lee, J. Chromatogr A. 1216 (2009) 701; Q. Xiao, C. Yu, J. Xing, B. Hu, J. Chromatogr A. 1125 (2006) 133—each incorporated herein by reference in its entirety). HFM-LPME is a fast, simple and inexpensive solvent minimized sample preparation method. The LPME combines extraction, sample cleanup and sample preconcentration in a single step. The porous HFM membrane acts as a filtering device that eliminates interfering particles. After extraction the clean extract is suitable for direct instrumental analyses. Thus, HFM-LPME has the potential for selective extraction of analytes from complex matrices. The technique is based on the distribution of analytes between microliter volumes of organic phase (acceptor phase) and the sample (donor phase).

The current disclosure describes a single step HFM-LPME for the determination of low and high concentrations of sulfur compounds in crude oils and diesel samples.

BRIEF SUMMARY OF THE INVENTION

The foregoing paragraphs have been provided by way of general introduction, and are not intended to limit the scope of the following claims. The described embodiments, together with further advantages, will be best understood by reference to the following detailed description taken in conjunction with the accompanying drawings.

One embodiment of the disclosure relates to a hollow fiber membrane supported liquid-phase microextraction (HFM-LPME) method for determining sulfur compound concentration in a hydrocarbon sample.

In another embodiment the method comprises mixing a hollow fiber filled with an organic solvent and the hydrocarbon sample to extract one or more sulfur containing compounds from the hydrocarbon sample into the organic solvent.

In another embodiment extraction, sample cleanup, and sample preconcentration occur in a single step.

In another embodiment the method comprises injecting the organic solvent into a gas chromatography-chemiluminescene detector to determine the amount of sulfur present in the hydrocarbon sample.

In another embodiment the solvent is a polar organic solvent selected from the group consisting of acetone, furfurol, furfuryl alcohol, and N-methylpyrrolidone.

In another embodiment the solvent is N-methylpyrrolidone.

In another embodiment the sulfur compounds are selected from the group consisting of 2,4-dimethylbenzothiopene, 2,6-dimethylbenzothiopene, 2,3-dimethylbenzothiopene, 2,3,6-trimethylbenzothiopene, 2,3,4-trimethylbenzothiopene, dibenzothiopene, 4-methyldibenzothiopene, 1-methyldibenzothiopene, 4,6-dimethyldibenzothiopene, 4-ethyldibenzothiopene, 3-methyldibenzothiopene, 2,4-dimethyldibenzothiopene, 3,6-dimethyldibenzothiopene, 2,8-dimethyldibenzothiopene, 1,4-dimethyldibenzothiopene, 1,3-dimethyldibenzothiopene, 4 ethyl, 6-methyl-dibenzothiopene, 2-methyldibenzothiopene, 2,4,8-trimethyldibenzothiopene, and 2-propo-dibenzothiopene.

In another embodiment the hollow fiber membrane has a pore size in the range of 0.1-0.5 μm.

In another embodiment the hollow fiber membrane has an inner diameter in the range of 500-700 μm.

In another embodiment the hollow fiber membrane has a wall thickness in the range of 100-300 μm.

In another embodiment extracting the analytes occurs over a time period in the range of 15-25 minutes.

In another embodiment extracting the analytes occurs over a time period of 20 minutes.

In another embodiment the hydrocarbon sample is crude oil.

In another embodiment the hydrocarbon sample does not include an aqueous phase.

In another embodiment the recovery is between 77 and 91%.

In another embodiment the disclosure relates to a hollow fiber membrane supported liquid-phase microextraction (HFM-LPME) system for determining sulfur compound concentration in a hydrocarbon sample.

In another embodiment the system comprises a liquid-phase microextractor comprising a hollow fiber membrane.

In another embodiment the hollow fiber membrane is filled with an organic solvent and a hydrocarbon sample to extract one or more sulfur containing compounds from the hydrocarbon sample into the organic solvent; and In another embodiment the system comprises a gas chromatography-chemiluminescene detector that determines the amount of sulfur present in the hydrocarbon sample after the sample is injected into the detector.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Referring now to the drawings, wherein like reference numerals designate identical or corresponding parts throughout the several views.

One embodiment of the disclosure relates to a hollow fiber membrane supported liquid-phase microextraction (HFM-LPME) method for determining sulfur compound concentration in a hydrocarbon sample.

In another embodiment of the disclosure a hollow fiber membrane is used as a filter to extract the analytes from the sample solution of crude oil. Preferably the hollow fiber membrane is a propylene hollow fiber membrane. The hollow fiber membrane has an inner diameter in the range of 200-800 Um, 300-700 μm, or 400-650 μm. Preferably the hollow fiber membrane has an inner diameter of 600 μm. The hollow fiber membrane has a wall thickness in the range of 50-350 μm, 100-300 μm, or 150-250 μm. Preferably the hollow fiber membrane has a wall thickness of 200 μm. The hollow fiber membrane has a wall pore size in the range of 0.05-2 μm, 0.1-1.5 μm, or 0.15-0.5 μm. Preferably the hollow fiber membrane has a wall pore size of 0.2 μm. The hollow fiber membrane has a length in the range of 5-25 cm, 10-20 cm, or 12-18 cm. Preferably the hollow fiber membrane has a length of 15 cm.

In another embodiment a sample solution of crude oil is spiked with sulfur compounds. The sulfur compounds contacted with the crude oil include but are not limited to 2,4-dimethylbenzothiopene, 2,6-dimethylbenzothiopene, 2,3-dimethylbenzothiopene, 2,3,6-trimethylbenzothiopene, 2,3,4-trimethylbenzothiopene, dibenzothiopene, 4-methyldibenzothiopene, 1-methyldibenzothiopene, 4,6-dimethyldibenzothiopene, 4-ethyldibenzothiopene, 3-methyldibenzothiopene, 2,4-dimethyldibenzothiopene, 3,6-dimethyldibenzothiopene, 2,8-dimethyldibenzothiopene, 1,4-dimethyldibenzothiopene, 1,3-dimethyldibenzothiopene, 4-ethyl-6-methyldibenzothiopene, 2-methyldibenzothiopene, 2,4,8-trimethyldibenzothiopene, and 2-propodibenzothiopene.

A sample of crude oil of a volume in the range of 1-9.5 mL, 2-9 mL, or 2-8 mL is transferred to a 10 mL vial. Preferably the sample has a volume of 4 mL. Once the sample is in the 10 mL vial, it is mixed with a stirring rod. A solvent is drawn into a syringe and inserted into the hollow fiber membrane. The solvent is a solvent that is immiscible in oil including but not limited to acetone, furfurol, furfuryl alcohol, N-methylpyrrolidone. Preferably the solvent is N-methylpyrrolidone. The solvent is drawn into a syringe at a volume in the range of 1-100 μL, 2-90 μL, or 5-50 μL. Preferably 10 μL of the solvent is drawn into the syringe and the syringe needle tip is inserted in the hollow fiber membrane. The sample is stirred in a range of 60-80 rad $s^{-1}$, 65-75 rad $s^{-1}$, or 68-74 rad $s^{-1}$. Preferably the sample is stirred at 73 rad $s^{-1}$. The sample is stirred for a time period in the range of 10-40 minutes, 15-30 minutes, or 18-25 minutes. Preferably the sample is stirred for 20 minutes.

Following extraction, the syringe-fiber assembly is removed from the sample and the acceptor solution is withdrawn from the fiber. The hollow fiber membrane is discarded. The extract with a volume in the range of 1-10 μL, 1.5-8 μL or 1.75-3 μL is injected into the gas chromatography-chemiluminescence detector. Preferably 2 μL of the extract is injected into the gas chromatography-chemiluminescence detector for analysis.

In one embodiment of the invention at least 75% of the analytes are recovered from the crude oil. In another embodiment at least 90% of the analytes are recovered from the crude oil.

In another embodiment no pretreatment of the crude oil sample is needed.

In another embodiment extracting, sample cleanup, and sample preconcentration occur in a single step.

In another embodiment the sample solution does not comprise an aqueous solution.

Examples

Figure 1:
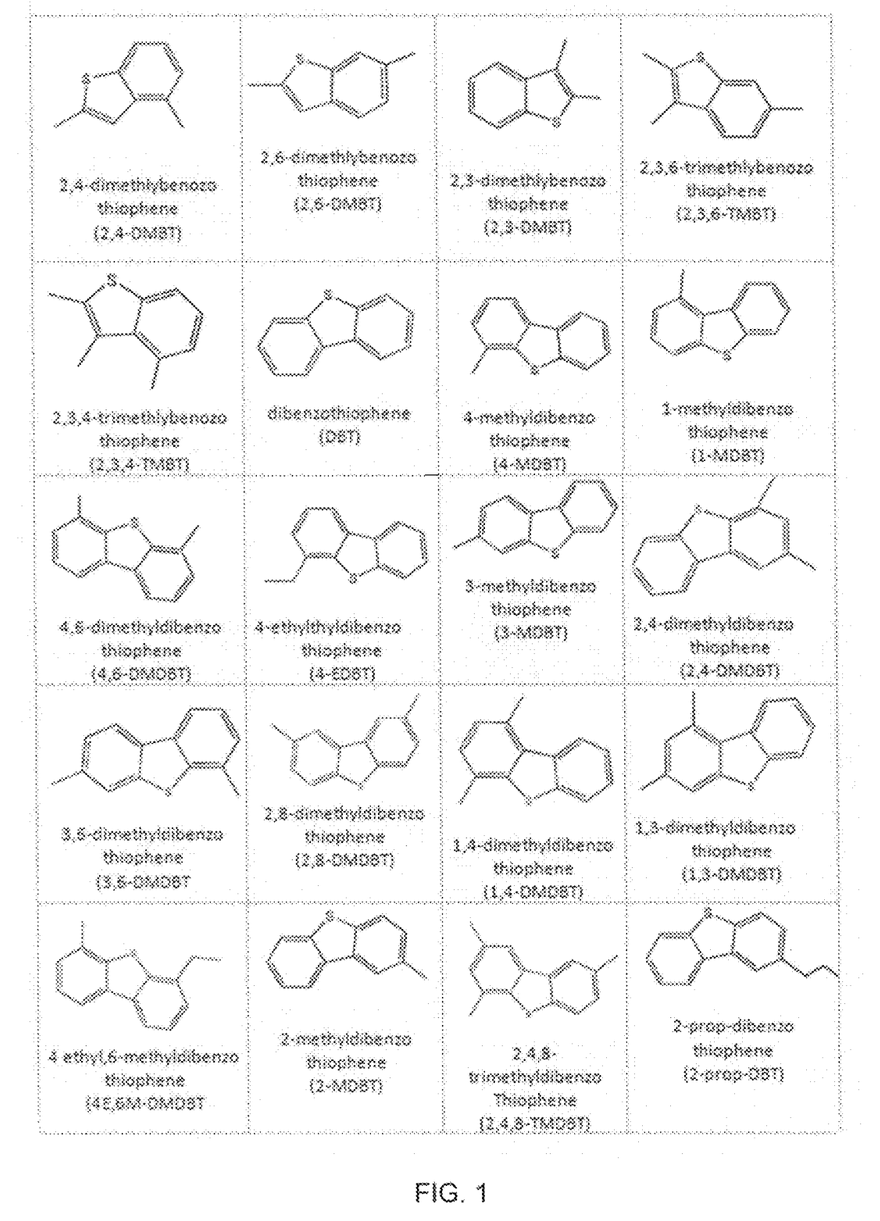
FIG. 1 depicts structures of sulfur compounds.

High purity nineteen sulfur compounds as shown in FIG. 1 were obtained from Sigma-Aldrich (St. Louis, Mo., USA) and have been used as model compounds. Various HPLC-grade organic solvents were purchased from Sigma-Aldrich to study the sulfur compound extraction. Q3/2 Accurel polypropylene hollow fiber membrane (600 μm inner diameter (I.D), 200 μm wall thickness and 0.2 μm wall pore size) was purchased from Membrana (Wuppertal, Germany). 15-cm lengths of HFM were used for extraction. Diesel, Arabian crude oils (light, medium and heavy) were received from Saudi Aramco, Saudi Arabia before desulfurization process. Standards were prepared using ultra low sulfur diesel (after treated with hydrodesulfurization at Saudi Aramco, concentration in the range between not detected and 0.25 μg $mL^{-1}$) with known concentration of target analytes Samples.

The API gravity and density of examined crude oil range from 27 to 33.0 and from 0.859 to 0.892 g $mL^{-1}$, respectively. The sulfur and nitrogen of crude oil ranging between 1.9 to 3.0 wt % and 810 to 1430 ppm respectively. Crude oil has also trace amount of vanadium and nickel 14 to 50 ppm and >18 μg $mL^{-1}$, respectively. Whereas, the heavy diesel has density of 0.8152 g $mL^{-1}$, 9 μg $mL^{-1}$ of nitrogen and sulfur content of 0.127%.

The LPME-HFM experimental conditions were set using middle distillate of diesel with spiked known concentrations of individual target analyte. Extractions were performed according to the following procedure: A 4-mL sample was transferred to the 10-Ml vial and a stirring bar was placed in it. Then, 10 μL of the desirable acceptor phase was drawn into a syringe. The syringe needle tip was inserted into a 5-cm hollow-fiber, and the acceptor solution was introduced into it. The (together with the needle tip) was immersed in the diesel (donor) sample. Samples were stirred at 73 rad $s^{-1}$ (700 rpm; 1 rpm=0.1047 rad $s^{-1}$) for 20 min. After extraction, the syringe-fiber assembly was removed from the sample. The acceptor solution was withdrawn from the fiber and then the HFM was discarded. 2 μL of the extract was injected into the gas chromatography-chemiluminesence detector.

ASTM D 5504 was used to determine the sulfur compounds in natural gas and gaseous fuels with GC-SCD detection. GC-SCD conditions were utilized from the ASTM method, more specifically the ASTM D 5623 method.

Sample analyses were carried out using a Agilent 7890A chromatograph (Agilent Technologies, USA) system equipped with a sulfur chemilumisence detector (GC-SCD), autosampler and a DB-1 fused silica capillary column 60 m×0.25 mm I. D., 0.25 μm film thickness (J & W Scientific, Folsom, Calif., USA). Helium was used as the carrier gas at a flow rate of 1.3 ml $min^{-1}$. Samples (2 μL) were injected in splitless mode with an injection time of 2 minutes. The injection temperature was set at 250° C., the SCD furnace temperature was 800° C. with 40 ml min-1 of Hydrogen and 40 ml min-1 of air. The GC-temperature program was as follows: initial temperature 40° C. (1 min, holding time), then increased by 5° C. $min^{-1}$ to 300° C. (10 min, holding time).

The extraction parameters affecting HFM-LPME such as the nature of solvents, ratios of solvent and sample and extraction time were set. The peak areas after extraction were used to determine the extraction performance.

Since the samples were diesel and crude oils, it was essential to choose a suitable immiscible solvent that can withstand for longer extraction time without leaking from the HFM during extraction. The organic solvents were selected based on the properties (i) high solubility of sulfur compounds in the extraction solvent, (ii) low boiling point and (iii) immiscible in petroleum product and (iv) compatibility with the HFM which is made of polypropylene and is hydrophobic (D. M. Abd El-Aty, O. I. Sif El-Din, S. I. Hassan, S. M. Tawfik, S. Hanafi, Pet. Sci. Technol. 7 (2009) 861—incorporated herein by reference in its entirety).

Figure 2A:
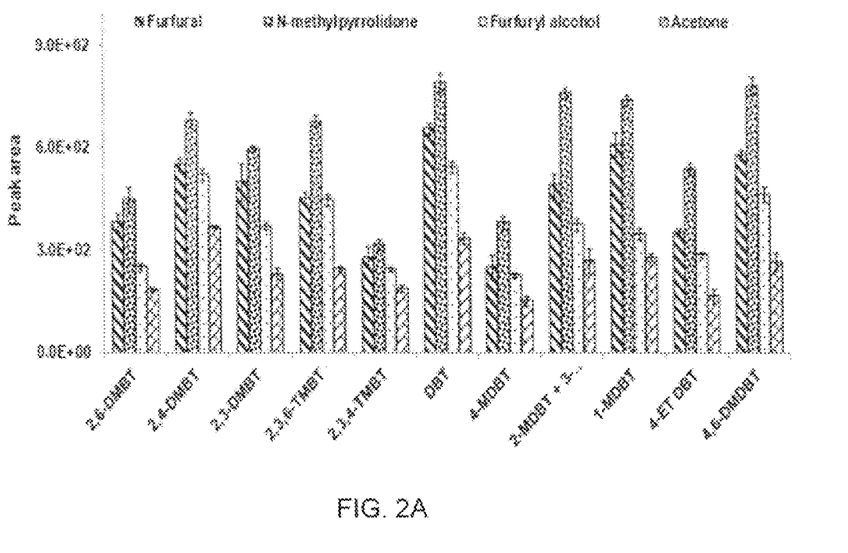
FIGS. 2A-2B are graphs of the extraction efficiency of different polar organic solvents used for HFM-LPME-GC-SCD analyses.
Figure 2B:
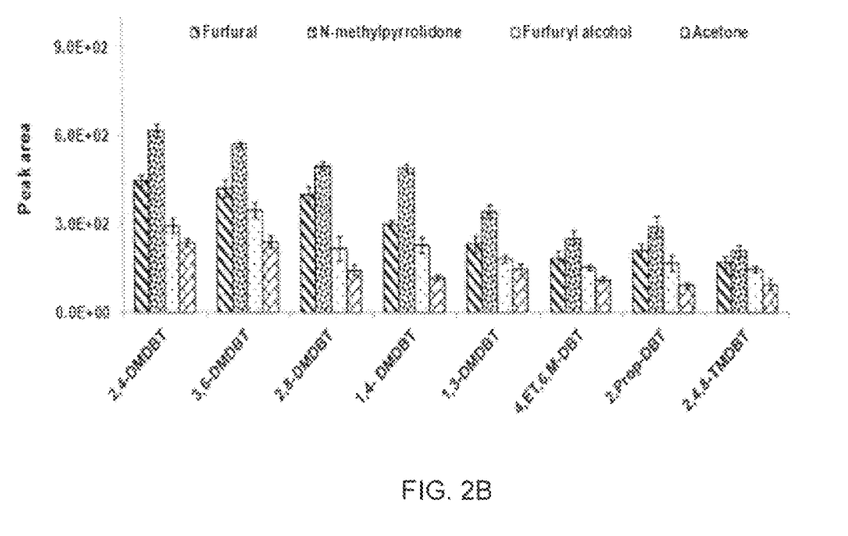

Polar organic solvents as acetone, furfurol, furfuryl alcohol and N-methylpyrrolidone are preferable. Extraction using N-methylpyrrolidone yielded comparatively higher response than other solvents as shown in FIG. 2A and FIG. 2B). FIG. 2A and FIG. 2B illustrate the extraction efficiency of different polar organic solvents used for HFM-LPME-GC-SCD analyses. Higher extraction efficiency of N-methylpyrrolidone is due to the enhanced polarity/polarizability of the solvent and the electrostatic interactions of the solvent with the analytes. Also N-methyl pyrrolidone has high thermal stability and is suitable for longer extraction time compared to other organic solvents. Further studies were conducted to select a suitable extraction solvent volume between 10 and 100 μL. As expected, lower solvent volume gave higher peak areas as compared to 100 μL. After each extraction 10 μL was transferred to GC vial insert and 2 μL was injected for analysis.

Figure 3A:
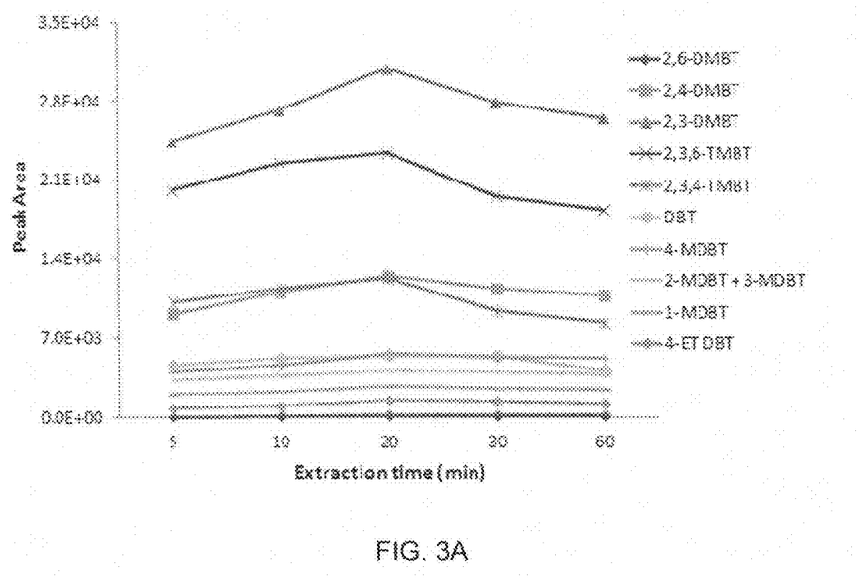
FIGS. 3A-3B are graphs of the HFM-LPME extraction time using N-methylpyrrolidone as an extraction solvent.
Figure 3B:
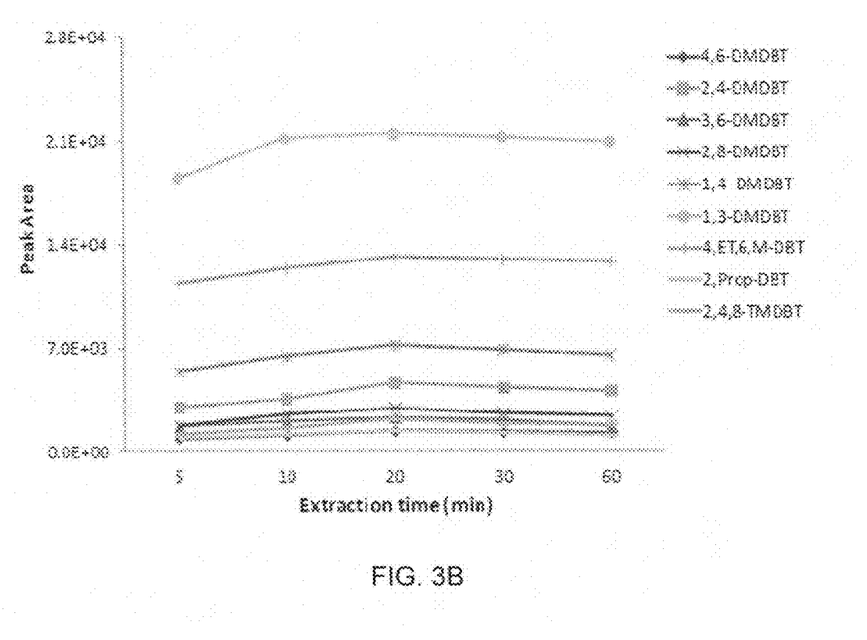

A series of extraction times were investigated by extracting diesel sample containing known amount $^P$of each analyte (nineteen sulfur compounds) at 73 rad s$^{-1}$ stirring speed. FIG. 3A and FIG. 3B shows the extraction time profiles with partition coefficients of HFM-LPME. Various extraction times from 5 to 60 min was evaluated with HFM-LPME. The results showed that the analyte response factors increased up to 20 min of extraction and then no significant additional increment in the extraction efficiency was observed as illustrated in FIG. 3A and FIG. 3B). FIG. 3A and FIG. 3B illustrate the influence of HFM-LPME extraction time using N-methylpyrrolidone as an extraction solvent.

To evaluate the practical applicability of the proposed HFM-LPME, linearity, repeatability and limits of detection relative recovery were investigated under optimized conditions. The GC peak area counts were plotted against the respective analyte concentrations to generate calibration curves. The calibration plots were linear over the range of 0.1 to 250 μg mL$^{-1}$ with coefficient of determination ($R^2$) between 0.985 and 0.999 for HFM-LPME. The limits of detection (LODs) for all target analytes were determined by progressively decreasing the concentrations of analytes until signals were just detected at a signal-to-noise ratio of 3 (S/N=3). The LODs ranged from 0.001 to 0.111 μg mL$^{-1}$ (Table 1). Three replicates were used to calculate LODs. The repeatability of GC peak areas was studied for three replicate experiments for a diesel sample. The relative standard deviations (RSDs) of all of the analytes for HFM-LPME were <14%. Table 1 is a quantitative analys of HFM-LPME-GC-SCD and Table 1 is shown below.

TABLE 1

Quantitaive Analysis of HFM-LPME-GC-SCD

| Sulfur analytes | Linearitty (μg mL$^{-1}$) | Coefficient of Determination ($R^2$) | Equation | RSD % (n = 3) | LODs (μg mL$^{-1}$) |
|---|---|---|---|---|---|
| 2,6-DMBT | 0.1-250 | 0.997 | Y = 1.902x + 0.077 | 10.2 | 0.033 |
| 2,4-DMBT | 0.1-250 | 0.998 | Y = 1.898x − 6.268 | 8.1 | 0.002 |
| 2,3-DMBT | 0.1-250 | 0.997 | Y = 1.832x − 5.120 | 12.3 | 0.002 |
| 2,3,6-TMBT | 0.1-250 | 0.998 | Y = 1.895x − 13.264 | 8.9 | 0.009 |
| 2,3,4-TMBT | 0.1-250 | 0.986 | Y = 1.869x + 9.136 | 9.5 | 0.012 |
| DBT | 0.1-250 | 0.998 | Y = 1.837x + 0.034 | 6.2 | 0.001 |
| 4-MDBT | 0.1-250 | 0.997 | Y = 1.788x − 1.923 | 8.2 | 0.020 |
| 2-MDBT + 3-MDBT | 0.1-250 | 0.998 | Y = 1.787x − 0.404 | 5.9 | 0.030 |
| 1-MDBT | 0.1-250 | 0.998 | Y = 1.772x + 1.034 | 8.2 | 0.038 |
| 4-ET DBT | 0.1-250 | 0.985 | Y = 1.746x − 8.119 | 10.1 | 0.021 |
| 4,6-DMDBT | 0.1-250 | 0.999 | Y = 1.775x + 4.822 | 4.5 | 0.015 |
| 2,4-DMDBT | 0.1-250 | 0.995 | Y = 1.817x + 0.497 | 10.8 | 0.012 |
| 3,6-DMDBT | 0.1-250 | 0.998 | Y = 1.803x + 0.022 | 11.3 | 0.047 |
| 2,8-DMDBT | 0.1-250 | 0.995 | Y = 1.808x + 2.188 | 10.8 | 0.021 |
| 1,4-DMDBT | 0.1-250 | 0.987 | Y = 1.738x + 2.418 | 13.3 | 0.021 |
| 1,3-DMDBT | 0.1-250 | 0.998 | Y = 1.7953x + 1.297 | 10.5 | 0.040 |
| 4,ET,6,M-DBT | 0.1-250 | 0.987 | Y = 1.825x + 5.664 | 13.8 | 0.021 |
| 2,Prop-DBT | 0.1-250 | 0.985 | Y = 1.870x + 9.695 | 11.6 | 0.111 |
| 2,4,8-TMDBT | 0.1-250 | 0.988 | Y = 1.866x − 8.445 | 11.7 | 0.050 |

Optimum conditions of HFM-LPME were applied to determine the sulfursulfur compounds ultra low sulfur diesel sample and only few sulfur analytes were detected (Table 2). To assess matrix effects on HFM-LPME, nineteen sulfur compounds were spiked in to the same sample at 1 μg mL$^{-1}$. The spiked samples were extracted using HFM-LPM and ASTM D 5504 methods, a separate instrumental calibration curves were established for ASTM D 5504 method quantification. Table 2 shows the recoveries obtained by HFM-LPEM and ASTM D 5504 methods. Table 2 is shown below.

TABLE 2

Extraction Recoveries Comparison Between HFM-LPME and ASTM D 5504 of 1 μg mL$^{-1}$ Spiked Ultra Low Sulfur in Diesel Samples (n = 3)

| Sulfur analyte | Ultra low sulfur in disel (used as blank sample) μg mL$^{-1}$ | HFM-LPME Recovery % | ASTM D 5504 Recovery % |
|---|---|---|---|
| 2,6-DMBT | 0.01 | 80 | 77 |
| 2,4-DMBT | ND | 87 | 80 |
| 2,3-DMBT | 0.03 | 81 | 78 |
| 2,3,6-TMBT | ND | 77 | 73 |
| 2,3,4-TMBT | ND | 81 | 76 |
| DBT | 0.05 | 91 | 85 |
| 4-MDBT | 0.05 | 82 | 79 |
| 2-MDBT + 3-MDBT | ND | 85 | 80 |
| 1-MDBT | 0.01 | 87 | 78 |
| 4-ET DBT | 0.01 | 77 | 75 |
| 4,6-DMDBT | 0.25 | 91 | 84 |
| 2,4-DMDBT | 0.01 | 89 | 87 |
| 3,6-DMDBT | 0.02 | 86 | 81 |
| 2,8-DMDBT | ND | 85 | 78 |
| 1,4-DMDBT | 0.25 | 86 | 80 |

TABLE 2-continued

Extraction Recoveries Comparison Between HFM-LPME and ASTM D 5504 of 1 µg mL$^{-1}$ Spiked Ultra Low Sulfur in Diesel Samples (n = 3)

| Sulfur analyte | Ultra low sulfur in disel (used as blank sample) µg mL$^{-1}$ | HFM-LPME Recovery % | ASTM D 5504 Recovery % |
|---|---|---|---|
| 1,3-DMDBT | 0.07 | 84 | 81 |
| 4,ET,6,M-DBT | ND | 79 | 75 |
| 2,Prop-DBT | ND | 82 | 78 |
| 2,4,8-TMDBT | ND | 80 | 75 |

The recoveries were between 77% and 91% for HFM-LPME and 75% and 85% for ASTM D 5504, respectively. Application of HFM-LPME method was applied to determine the sulfur compounds in Arabian crude oil samples. Table 3 shows the concentrations of sulfur compounds detected in Arabian crude oil samples between HFM-LPME and ASTM D 5504. Table 3 is shown below.

| Sulfur analyte | *Concentration of sulfur species in crude oils (ASTM D 5504) (µg mL$^{-1}$) (n = 3) | | | Concentration of sulfur species in crude oils (using HF-LPME) (µg mL$^{-1}$) (n = 3) | | |
|---|---|---|---|---|---|---|
| | Arabian Light | Arabian Medium | Arabian Heavy | Arabian Light | Arabian Medium | Arabian Heavy |
| 2,6-DMBT | 43 | 54 | 65 | 52 | 67 | 75 |
| 2,4-DMBT | 105 | 114 | 127 | 115 | 129 | 140 |
| 2,3-DMBT | 156 | 177 | 189 | 175 | 198 | 210 |
| 2,3,6-TMBT | 128 | 144 | 169 | 142 | 154 | 187 |
| 2,3,4-TMBT | 116 | 136 | 147 | 127 | 149 | 163 |
| DBT | 62 | 87 | 117 | 74 | 95 | 129 |
| 4-MDBT | 53 | 60 | 85 | 57 | 74 | 105 |
| 2-MDBT + 3-MDBT | 47 | 56 | 76 | 59 | 70 | 88 |
| 1-MDBT | 27 | 35 | 48 | 40 | 40 | 56 |
| 4-ET DBT | 58 | 67 | 80 | 67 | 78 | 94 |
| 4,6-DMDBT | 68 | 93 | 110 | 74 | 110 | 127 |
| 2,4-DMDBT | 14 | 21 | 28 | 17 | 32 | 33 |
| 3,6-DMDBT | 66 | 79 | 98 | 82 | 97 | 115 |
| 2,8-DMDBT | 35 | 45 | 55 | 44 | 55 | 60 |
| 1,4-DMDBT | 28 | 34 | 38 | 34 | 39 | 42 |
| 1,3-DMDBT | 16 | 23 | 29 | 19 | 27 | 32 |
| 4,ET,6,M-DBT | 17 | 20 | 38 | 21 | 23 | 43 |
| 2,Prop-DBT | 19 | 26 | 32 | 23 | 31 | 39 |
| 2,4,8-TMDBT | 12 | 17 | 22 | 14 | 19 | 27 |

Figure 4:
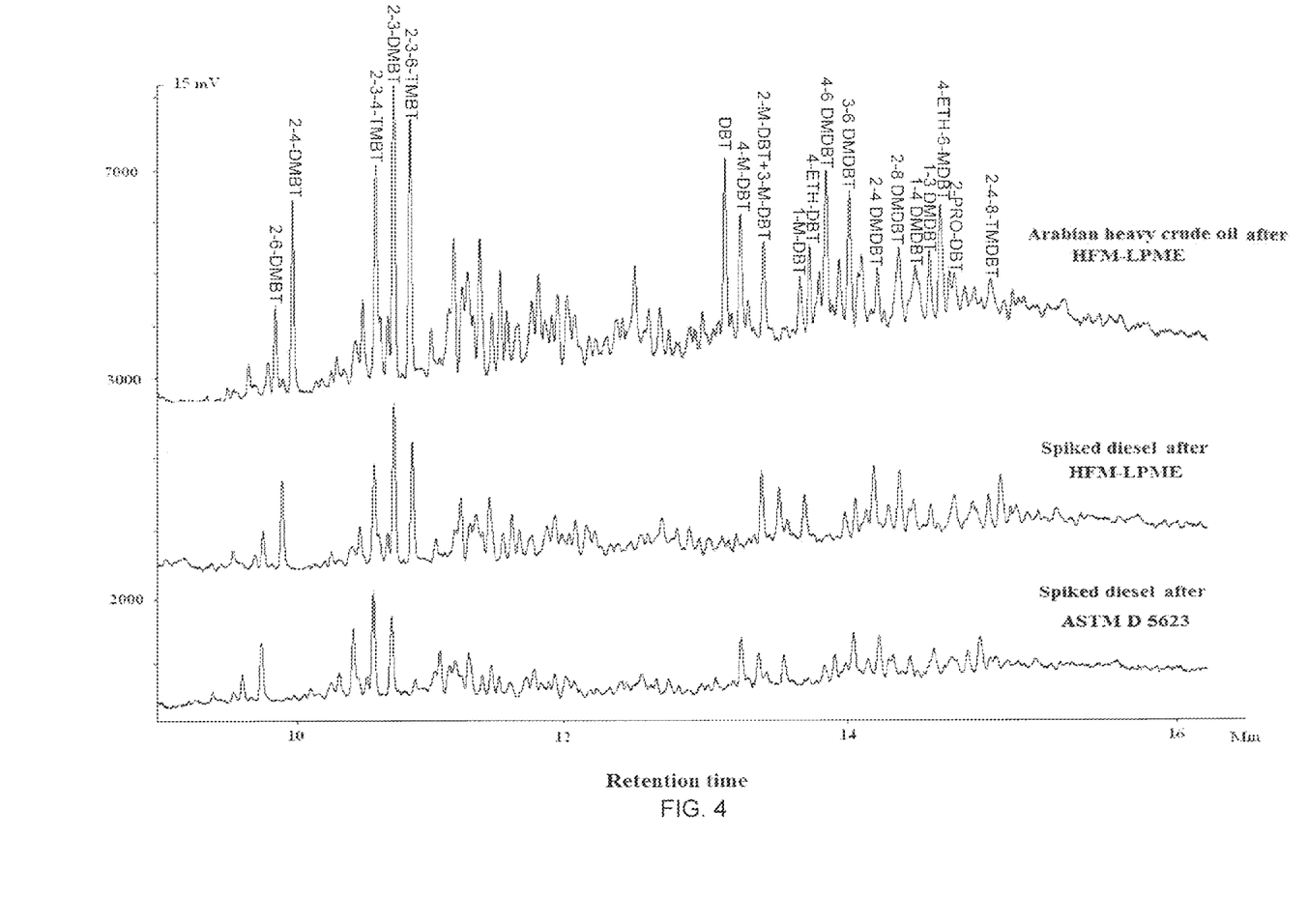
FIG. 4 is a chromatogram of HFM-LPME extraction of arabian crude oil, ultra low sulfur in diesel sample, and ultra low sulfur in diesel sample after ASTM D 5504 method.

FIG. 4 shows the comparison chromatogram of ASTM D 5504 and HFM-LPME of spiked diesel samples and HFM-LPME extracted chromatogram after Arabian crude oil sample. FIG. 4 illustrates the HFM-LPME extracted Chromatograms after (a) Arabian crude oil, (b) 1 µg mL$^{-1}$ spiked ultra low sulfur in diesel sample and (c) spiked ultra low sulfur in diesel sample after ASTM D 5504 method. The recoveries obtained by HFM-LPME for samples of diesel and crude oil were better and there was clear evidence of no matrix effect by the crude oil samples.

In comparison with ASTM D 5504 method, HFM-LPME gave better sensitivity for the determination of sulfur compounds in the complex petroleum matrices and the HFM-LPME has a distinct advantage. The enhancement of extraction efficiency afforded by the polar solvent provides for potential applications to the direct determination of sulfur compounds in complex diesel and crude oil samples without any further pretreatment. An efficient liquid phase microextraction (LPME) method was developed for the determination of sulfur compounds in crude oils and its fractions (e.g diesel). A wide range of sulfur compounds including benzothiophene, dibenzothiophene and their derivatives were used as model compounds for extraction. After extraction, the analyses were performed by gas chromatography equipped with sulfur chemiluminescence detector (GC-SCD). Various experiment conditions influencing the extraction such as extraction times, extraction solvents, solvent volume and quantitative parameters were optimized to achieve higher extraction efficiency and high accuracy. Under the optimized conditions, linearity was evaluated between 0.1 and 250 µg mL$^{-1}$ and higher correlation of determination ($R^2$) ranging between 0.9856 to 0.9999 were obtained. The reproducibility was calculated were in the range of 77 and 91%. The conditions were applied to the determination of sulfur compounds in crude oil (Arabian light, Arabian medium and Arabian heavy) and diesel. Reference samples were used to calculate the recoveries and the results obtained were compared with conventional ASTM D5504 method.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, define, in part, the scope of the foregoing claim terminology such that no inventive subject matter is dedicated to the public.

The invention claimed is:

1. A hollow fiber membrane supported liquid-phase microextraction (HFM-LPME) method for determining sulfur compound concentration in a hydrocarbon sample, comprising:
   mixing a hollow fiber filled with an organic solvent and the hydrocarbon sample;
   extracting one or more sulfur containing compounds from the hydrocarbon sample into the organic solvent to form an analyte-containing solvent; and
   injecting the analyte-containing solvent into a gas chromatography-chemiluminescene detector to determine the amount of sulfur present in the hydrocarbon sample.

2. The method of claim 1 in which the solvent is a polar organic solvent selected from the group consisting of acetone, furfurol, furfuryl alcohol, and N-methylpyrrolidone.

3. The method of claim 2 in which the solvent is N-methylpyrrolidone.

4. The method of claim 1 in which the sulfur compounds are selected from the group consisting of 2,4-dimethylbenozothiopene, 2,6-dimethylbenozothiopene, 2,3-dimethylbenozothiopene, 2,3,6-trimethylbenozothiopene, 2,3,4-trimethylbenozothiopene, dibenzothiopene, 4-methyldibenzothiopene, 1-methyldibenzothiopene, 4,6-dimethyldibenzothiopene, 4-ethyldibenzothiopene, 3-methyldibenzothiopene, 2,4-dimethyldibenzothiopene, 3,6-dimethyldibenzothiopene, 2,8-dimethyldibenzothiopene, 1,4-dimethyldibenzothiopene, 1,3-dimethyldibenzothiopene, 4-ethyl-6-methyldibenzothiopene, 2-methyldibenzothiopene, 2,4,8-trimethyldibenzothiopene, and 2-propo-dibenzothiopene.

5. The method of claim 1, wherein:
   the hollow fiber membrane has a pore size in the range of 0.1-0.5 µm;

the hollow fiber membrane has an inner diameter in the range of 500-700 μm; and the hollow fiber membrane has a wall thickness in the range of 100-300 μm.

6. The method of claim 1 wherein extracting the analytes occurs over a time period in the range of 15-25 minutes.

7. The method of claim 6 wherein extracting the analytes occurs over a time period of 20 minutes.

8. The method of claim 1 in which the hydrocarbon sample is crude oil.

9. The method of claim 1 wherein extracting, sample cleanup, and sample preconcentration occur in a single step.

10. The method of claim 1 in which the recovery is between 77 and 91%.

11. A hollow fiber membrane supported liquid-phase microextraction (HFM-LPME) system for determining sulfur compound concentration in a hydrocarbon sample, comprising:
   a liquid-phase microextractor comprising a hollow fiber membrane;
      wherein the hollow fiber membrane is filled with an organic solvent and a hydrocarbon sample to extract one or more sulfur containing compounds from the hydrocarbon sample into the organic solvent to form an analyte-containing solvent; and
   a gas chromatography-chemiluminescene detector that determines the amount of sulfur present in the hydrocarbon sample after the analyte-containing solvent is injected into the detector.

12. The system of claim 11 in which the solvent is a polar organic solvent selected from the group consisting of acetone, furfurol, furfuryl alcohol, and N-methylpyrrolidone.

13. The system of claim 12 in which the solvent is N-methylpyrrolidone.

14. The system of claim 11 in which the sulfur compounds are selected from the group consisting of 2,4-dimethylbenozothiopene, 2,6-dimethylbenozothiopene, 2,3-dimethylbenozothiopene, 2,3,6-trimethylbenozothiopene, 2,3,4-trimethylbenozothiopene, dibenzothiopene, 4-methyldibenzothiopene, 1-methyldibenzothiopene, 4,6-dimethyldibenzothiopene, 4-ethyldibenzothiopene, 3-methyldibenzothiopene, 2,4-dimethyldibenzothiopene, 3,6-dimethyldibenzothiopene, 2,8-dimethyldibenzothiopene, 1,4-dimethyldibenzothiopene, 1,3-dimethyldibenzothiopene, 4-ethyl-6-methyldibenzothiopene, 2-methyldibenzothiopene, 2,4,8-trimethyldibenzothiopene, and 2-propo-dibenzothiopene.

15. The system of claim 11, wherein:
   the hollow fiber membrane has a pore size in the range of 0.1-0.5 μm;
   the hollow fiber membrane has an inner diameter in the range of 500-700 μm; and
   the hollow fiber membrane has a wall thickness in the range of 100-300 μm.

16. The system of claim 11 wherein extraction of the analytes occurs over a time period in the range of 15-25 minutes.

17. The system of claim 16 wherein extraction of the analytes occurs over a time period of 20 minutes.

18. The system of claim 11 in which the hydrocarbon sample is crude oil.

19. The system of claim 11 in which the hydrocarbon sample does not include an aqueous solution.

20. The system of claim 11 in which the recovery is between 77 and 91%.

* * * * *